United States Patent [19]

Heslin

[11] Patent Number: 4,527,294
[45] Date of Patent: Jul. 9, 1985

[54] INTRAOCULAR LENS CONSTRUCTION

[76] Inventor: K. B. Heslin, 36 E. 36th St., New York, N.Y. 10016

[21] Appl. No.: 562,078

[22] Filed: Dec. 16, 1983

Related U.S. Application Data

[63] Continuation-in-part of Ser. No. 512,312, Jul. 8, 1983, abandoned, which is a continuation of Ser. No. 392,511, Jun. 28, 1982, abandoned, which is a continuation of Ser. No. 218,694, Dec. 22, 1980, abandoned.

[51] Int. Cl.³ ............................ A61F 1/16; A61F 1/24
[52] U.S. Cl. .................................. 623/6; 128/303 R; 206/5.1; 206/210
[58] Field of Search .................. 3/13; 128/303 R; 206/5.1, 205, 210

[56] References Cited

U.S. PATENT DOCUMENTS

| 4,014,049 | 3/1977 | Richards et al. | 3/13 |
| 4,118,808 | 10/1978 | Poler | 3/13 |
| 4,122,556 | 10/1978 | Poler | 3/13 |
| 4,159,546 | 7/1979 | Shearing | 3/13 |
| 4,190,049 | 2/1980 | Hager et al. | 3/13 |
| 4,249,271 | 2/1981 | Poler | 3/13 |
| 4,257,521 | 3/1981 | Poler | 3/13 |

Primary Examiner—Ronald L. Frinks
Attorney, Agent, or Firm—Toren, McGeady, Stanger, Goldberg & Kiel

[57] ABSTRACT

An intraocular lens includes a lens body and a plurality of flexible haptics angularly spaced around the periphery of the lens body. The normally extended haptics are capable of being compressed towards the lens body and detachably held thereon, so that the haptics are essentially within the confines of the lens body, thereby reducing the overall dimension of the lens. A manipulator may be detachably secured to the lens body to facilitate handling and positioning of the lens within the eye.

20 Claims, 12 Drawing Figures

INTRAOCULAR LENS CONSTRUCTION

CROSS REFERENCE TO RELATED APPLICATIONS

This is a continuation-in-part of copending application Ser. No. 512,312, filed July 8, 1983, now abandoned, which is a continuation of application Ser. No. 392,511, filed June 28, 1982, now abandoned, which was a continuation of application Ser. No. 218,694, filed Dec. 22, 1980, now abandoned.

BACKGROUND OF THE INVENTION

1. Field of the Invention:

The invention generally relates to intraocular lenses and is particularly directed to an intraocular lens implant assembly for facilitating insertion and positioning, as well as general handling, of the lens during surgery.

2. Background Information:

Intraocular lenses are widely used for the correction of aphakia, to wit, lack of the human crystalline lens. Following the removal of a cataract by any of the known techniques, such as intracapsular, extracapsular, phacoemulsification and other known methods, intraocular lenses are positioned for optical correction to replace the human lens and to stay within the eye as a permanent implant.

A variety of intraocular lens designs have previously been proposed, as evidenced by the disclosures in the prior art patents listed below. These lens designs vary both with regard to the shape and configuration of the optical lens body proper and the mounting or fixational means for enabling the lens body permanently to remain in a fixed and stable position within the eye. Generally, known intraocular lens constructions comprise an optical lens body proper, usually composed of a suitable plastic or glass, and a number of mounting legs or fixation members attached to the lens body and generally referred to in the profession as haptics. The haptics are usually flexible and of plastic and extend away from the lens body. In the ultimate position of the lens body, the haptics contact and bear against portions of the eye anatomy, thereby supporting the lens body in a stable and permanent position.

Considering the extremely small size of such lens constructions, it will be appreciated that considerable dexterity is required of the surgeon to manipulate, insert and position the lens construction within the eye. In order to assist the surgeon in this respect, a variety of instruments and tools have previously been proposed and used to facilitate implantation of the artificial lens into the eye in a manner avoiding or reducing complications or damage to the eye. Various surgical techniques thus allow the surgeon at the operating table to remove a sterile intraocular lens from a package and to prepare and affix it in some suitable way to an insertional device such as, for example, forceps. After the lens has thus been gripped by the tool, the surgeon inserts the lens into the eye through a suitable corneoscleral incision and, in some insertional methods, through the pupil. Since the haptics, by necessity, normally extend away from the lens body proper, they have, of course, a tendency to interfere with both the insertion and the subsequent positioning of the lens and may even damage eye tissue during the manipulation. Moreover, the extended haptics require a larger incisional opening than would be required if the haptics were not to extend away from the lens body. Some surgeons have attempted to overcome some of the difficulties described above by "loading" at least one of the haptics during surgery and prior to insertion of the lens into the eye, by compressing the haptic in a direction towards the lens body. This is done with the help of an insertional device which thus pushes the haptic onto the lens body while the lens is inserted. This, however, requires manual dexterity of considerable extent which more often than not exceeds the skill possessed by the surgeon.

In addition, such pre-insertion manipulations increase the danger of contamination and dropping of both the lens and the insertional device. Further, such procedures may result in improper fixation of the lens and in breakage of either the lens or the haptics.

3. Description of the Prior Art:

The following patents relate to intraocular lens constructions and/or methods for positioning such lenses within the eye. However, none of these patents discloses or suggests an intraocular lens assembly of the kind disclosed and claimed herein.

U.S. Patents Nos.:
  4,056,855
  4,092,743
  4,159,546
  4,014,049
  3,991,426
  4,053,953
  3,866,249
  4,118,808
  4,122,556
  4,257,521
  4,190,049
  4,249,271

OBJECTS OF THE INVENTION

It is the primary object of the present invention to provide an intraocular lens construction which facilitates handling, insertion and positioning of the lens during surgery.

It is another object of the present invention to provide an intraocular lens assembly which enables insertion of the lens into the eye in a safe and readily accomplished manner and through a smaller incision than has previously been possible.

Another object of the invention is to provide an intraocular lens construction which may be readily inserted through the pupil.

Another object of the present invention is to provide a prepackaged intraocular lens assembly which effectively prevents contamination during surgery.

Generally, it is an object of the invention to improve on the art of intraocular lens constructions and the manner in which they are to be implanted into the eye, as hitherto practiced.

SUMMARY OF THE INVENTION

Briefly, and in accordance with the invention, an intraocular lens construction comprises a lens body or "optic" of a suitable plastic, glass or the like, and a plurality of flexible, spaced haptics. One end of each haptic is permanently attached to the lens body near its periphery, while the other, free end of each haptic which, normally, extends away from the lens body, is capable of being "loaded" or compressed onto the lens body and temporarily held thereon by suitable holding means, so that the overall dimension of the lens construction is essentially that of the lens body proper.

The haptics, while being held in the loaded condition essentially within the confines of the lens body proper, are inserted in this condition through the incision in the eye, and, when applicable, through the pupil, and are only thereafter released or expanded by the surgeon to come into contact with the surrounding eye anatomy in a controlled manner, so that the surgeon can position and fix the lens construction without being hampered by interfering haptics.

It has been found that particularly excellent results are achieved if three equiangularly spaced haptics are used, which, preferably, are of arcuate shape. This results essentially in self-centering of the implant within spaces of varying sizes as they exist in the normal variations of the human eye.

In a preferred embodiment, the haptics are loaded in a direction towards and onto the lens body proper by a string or thread, properly looped through engagement means on the individual haptics and by pulling the string so that all the haptics are drawn onto the lens body in the desired manner. The end of the string or thread is then temporarily engaged in a catch on the lens body from which the string can be gradually released by the surgeon when the haptics are intended to be expanded again. If the surgeon should find that the position of the lens within the eye has to be adjusted, he may again "load" the haptics by pulling the string, prior to the adjustment procedure.

In other embodiments, the haptics are detachably engaged in slots or holes on the lens body during insertion and positioning of the lens.

Some eye surgeons prefer lens constructions in which only one of the haptics is subject to the loading manipulation. In such instances, the eye surgeon will usually use lenses with two haptics only, although it is possible to use three haptics as well. The invention also encompasses such embodiments.

Considered from another aspect, the invention also provides for a manipulator or insertional device which is detachably locked to the lens body during insertion and positioning and which is removed from the lens body after the lens has been positioned. The lens and the manipulator are packaged together as a unit, so that the surgeon during surgery merely has to remove the entire assembly from a casing or box in which the assembly is maintained in a sterile condition.

In a preferred embodiment, the haptics are loaded in the manner previously explained with the loading string having an end portion which is detachably secured to the manipulator. After the surgeon has inserted the lens through the incision in the eye and, when applicable, through the pupil, he thus detaches the string from the manipulator and permits the haptics, slowly and in a controlled and reversible manner, to expand into the desired contact position within the eye, whereupon the string is cut and removed and the manipulator detached from the lens body.

In order not to affect the capacity of the haptics to expand into their normal position away from the lens body, the "loading" should be carried out by the surgeon just prior to insertion into the eye. However, if the flexibility "memory" of the haptics is not affected by prolonged periods of storage of the haptics in compressed or loaded condition, the loading may be done by the manufacturer prior to packaging and shipping. Whether or not the loading will be effected at the time of manufacture or at the time of surgery is thus dependent upon the memory characteristics of the particular plastic of which the haptics are produced.

DETAILED DESCRIPTION OF THE DRAWINGS

Figure 1:
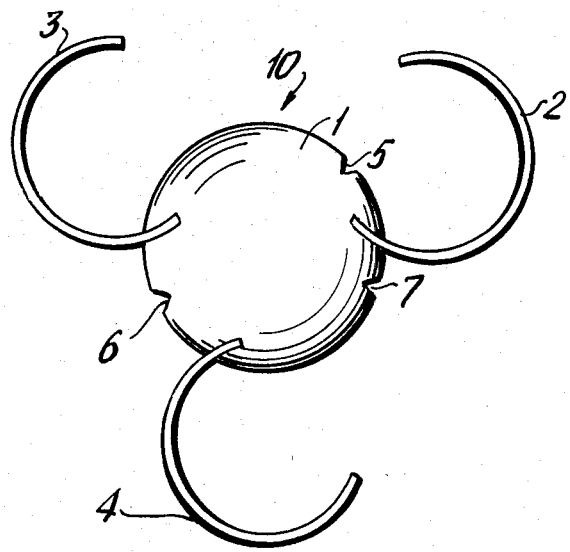
FIG. 1 is a plan view of a first embodiment of a lens with the legs or haptics in their normal, expanded position.

The lens construction shown in FIG. 1, and generally indicated by reference numeral 10, is adapted for posterior chamber implantation and comprises a plano-convex lens body 1, usually referred to in the profession as "optic", as well as three equiangularly spaced legs or haptics 2, 3 and 4. Although a plano-convex lens body is shown, it could instead be biconvex or convex-plano. One end of each haptic is permanently secured to the lens body 1, near its periphery in a suitable manner, while the other, free end of each haptic projects from the lens body.

It has been found that the provision of three equiangularly spaced haptics has considerable advantages since such design facilitates the self-centering of the lens within the available space of the eye and results in stable positioning. Three catch-like indentations or grooves 5, 6 and 7 are cut into the lens body at its periphery. For insertion purposes, the haptics are compressed or "loaded" so that the lens construction assumes the condition of FIG. 2, wherein each haptic engages a respective catch or groove, thereby significantly reducing the overall dimensions of the lens construction. After the surgeon has inserted the lens into the eye with the haptics in loaded condition, he pushes out the free ends of the haptics from their catches with a suitable instrument, thereby permitting the haptics to expand. As stated, the loading may be done just prior to insertion, or—the memory characteristics of the haptic material permitting—at the time of the manufacture of the lens construction.

Figure 2:
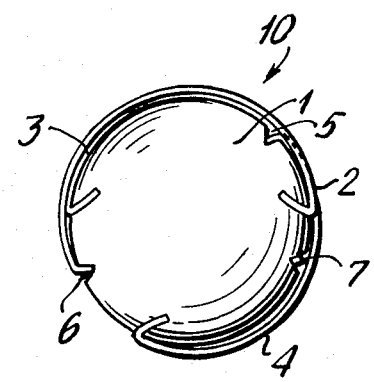
FIG. 2 shows the lens of FIG. 1 with the haptics in compressed or "loaded" condition in which the haptics are detachably held in peripheral slots or grooves.
Figure 3:
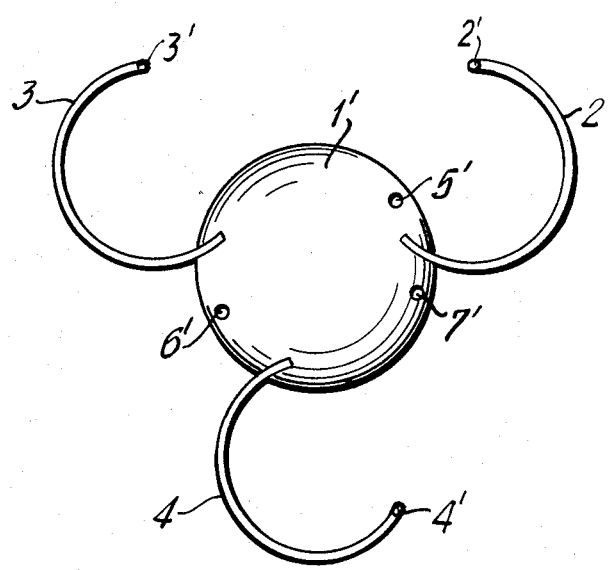
FIG. 3 is a plan view of a second embodiment in which the peripheral slots are replaced by holes in the lens body and the haptics are provided with complementary protrusions or "bumps"

The embodiment of FIG. 3 is similar to that of FIGS. 1 and 2. The catches 5, 6 and 7, however, are replaced by holes 5', 6' and 7' in the lens body 1' near its periphery and the haptics, near their free ends, are provided with upstanding protrusions or "bumps" 2', 3' and 4'. When the haptics are to be "loaded", they are bent until the bumps snap into the associated holes. To permit the haptics to expand, the surgeon pushes the bumps out of the holes.

Figure 4:
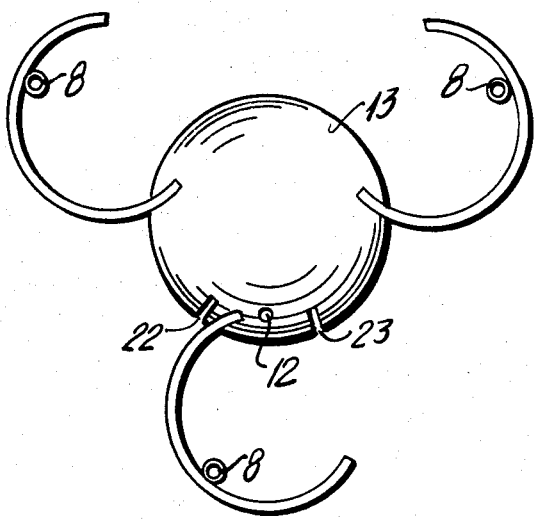
FIG. 4 is a plan view of a third embodiment of a lens construction.
Figure 5:
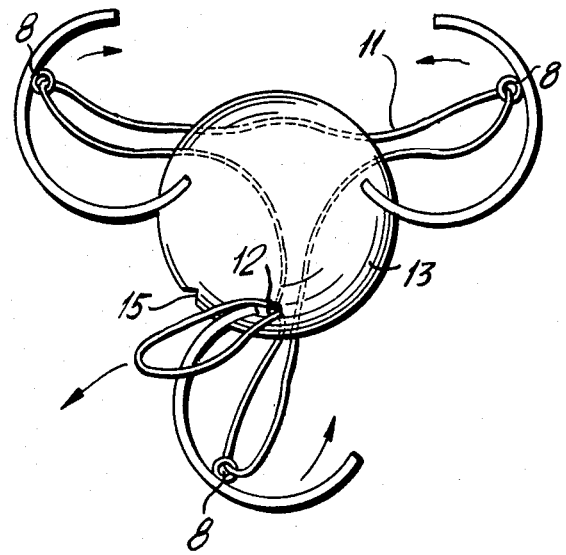
FIG. 5 shows the lens of FIG. 4 with the haptics in the process of being "loaded" by pulling them with a string or thread towards the lens body proper.
Figure 6:
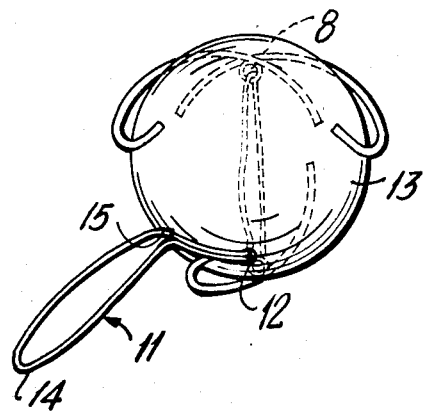
FIG. 6 shows a lens, without casing, after the pulling of the haptics towards and onto the lens body has been completed, with the string engaging a catch to hold and maintain the haptics in the pulled position.

Turning now to the embodiment of FIGS. 4-6, each arcuate haptic comprises an eyelet member. One of the eyelet members is indicated by reference numeral 8. The haptics, as in the previous embodiments, serve as the fixational members when the lens construction is positioned within the eye for implantation purposes. A string or thread 11, is looped through the eyelet members 8 and through a hole 12 in the lens body 13 (see FIG. 5) so that, upon pulling the thread, the three haptics are drawn towards and onto one surface of the lens body 13. When the pulling has been completed, all three haptics are then substantially within the confines or space defined by the periphery of the lens body 13, with only a minor portion protruding beyond the lens body periphery. This is shown more particularly in FIG. 6 wherein the looped end portion 14 of the string 11 is temporarily locked in a catch 15 provided in the peripheral rim portion of the lens body 13. In this manner, the flexible haptics are held and maintained in their pulled or "loaded" position, with only a minor portion of each haptic projecting beyond the confines of the lens body.

Figure 7:
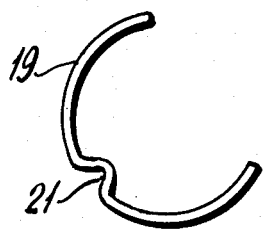
FIG. 7 shows a further embodiment of a haptic.

Instead of using eyelet members 8, the string may engage in a different type of engaging means. This is shown in FIG. 7 which illustrates a different embodiment of a single haptic 19 wherein the eyelet member of FIG. 4 has been replaced by a catch-like indentation 21. The indentation 21 is capable of supporting and guiding a string such as the string 11 during looping and pulling.

It should be appreciated that the invention is not limited to the particular lens constructions here shown. These particular embodiments are merely examples. There are many known forms for both the optical lens body and, particularly, the haptics, dependent on their ultimate location within the eye, to wit, for use in anterior, prepupillary, pupillary, and posterior chamber locations. The particular designs here shown, having three equiangularly spaced haptics, are intended to be self-centering within the available space in the eye when the haptics are in their ultimate position and contact and bear on the selected portions within the eye.

Since the overall size of the lens constructions of FIGS. 2 and 6 is significantly reduced, if compared to that of FIGS. 1, 3 and 4 in which the haptics are in their normal, expanded position, the size of the incision in the eye for inserting the lens construction may thus be significantly reduced which, of course, is of great advantage. It is well known that operating through minimal incisions helps to prevent collapse of the eye during surgery and affords greater surgical safety. Moreover, if a lens constructions, such as shown in FIG. 1, is inserted and then positioned by the surgeon with the haptics in their expanded position in which they extend away from the lens body proper, there is the distinct danger that the haptics may damage, or scratch, sensitive tissue and parts of the eye anatomy during the insertion and positioning procedures. This holds particularly true if the lens is also inserted through the pupil. The invention successfully obviates these drawbacks. Furthermore, if the lens construction were to be inserted with the haptics extending away from the lens body, the ultimate positioning is rendered more difficult since the expanded haptics have a tendency to interfere with the placement of the lens body within the confined space available. By contrast, by using a construction as shown in FIG. 6, the surgeon, with a suitable instrument such as a tweezer-like tool, will pull out the looped string end 14 from its engagement with the catch 15, to permit the haptics slowly to expand in a controlled manner, once the lens body has been placed in its ultimate position. The haptics will then slowly find their seat on the surrounding tissue, thereby accomplishing ultimate fixation of the lens construction. If adjustment of the lens position is desired, the surgeon may again "load" the haptics by pulling the string, whereupon the relocation is effected. Once the lens body with the haptics is in the correct position, the surgeon merely has to cut the string and pull it out through the incision in the eye.

Figure 8:
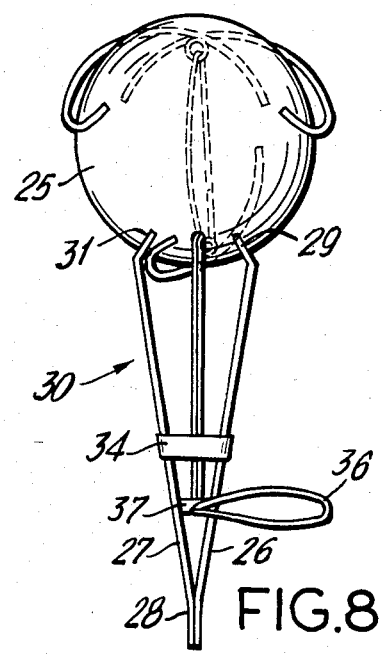
FIG. 8 is a view essentially corresponding to that of FIG. 6, wherein the haptics are in compressed or loaded position underlying the lens body, the lens assembly also including a manipulator detachably locked to the lens body with the string end being attached to the manipulator instead of to the lens body.
Figure 9:
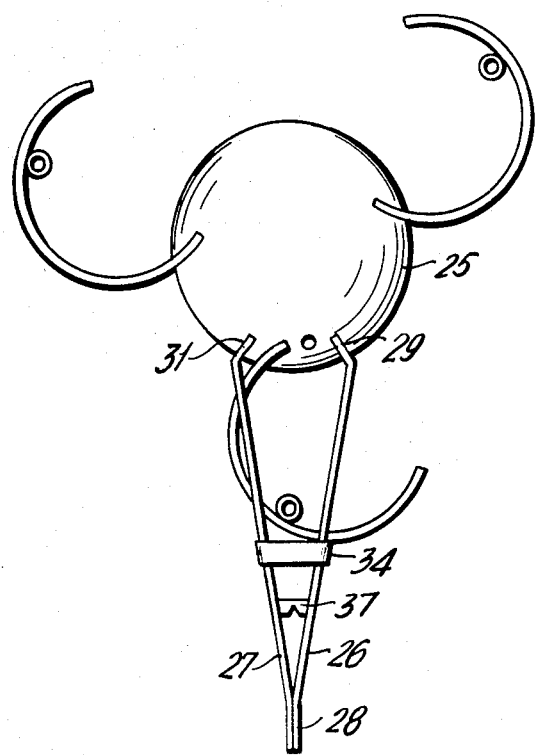
FIG. 9 shows the lens assembly of FIG. 8 after the string has been cut and removed and the haptics thus have expanded.
Figure 10:
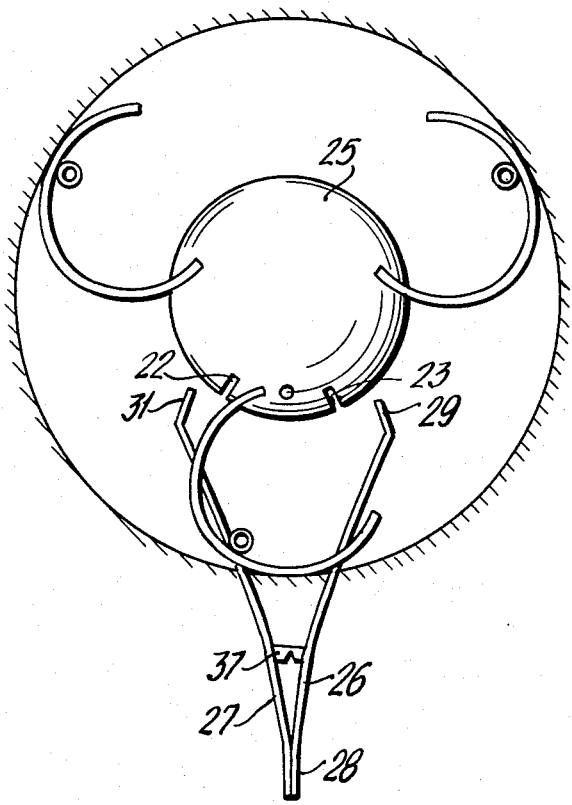
FIG. 10 shows the lens assembly of FIG. 8 after detachment of the manipulator with the lens securely positioned within the eye.
Figure 11:
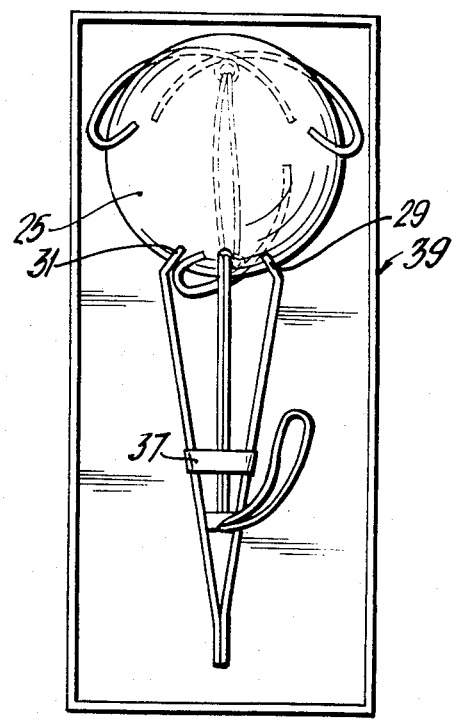
FIG. 11 shows the prepackaged lens assembly of FIG. 8 within a suitable box or casing, to allow for sterilization.

Turning now to the second aspect of the invention, as shown in FIGS. 8, 9 and 10, the lens of these figures is of the same construction as that of FIGS. 4-6. However, the lens body is provided with two angularly oriented grooves or indentations 22 and 23 (see also FIG. 4) extending from the periphery of the lens body 25 and being sufficiently short so as not to interfere with the optical characteristics of the lens body. A manipulator, generally indicated by reference numeral 30, is detachably connected to the lens body 25 during insertion and positioning of the latter. The manipulator 30 comprises two prong members 26 and 27 which are connected to each other at one end, as shown by reference numeral 28, while each free end of the prong members has angularly oriented tip portions 29 and 31 which are complementarily oriented to the grooves or identations 22 and 23 of the lens body and engage therein so as to be temporarily locked to the lens. The prong members 26 and 27 of the manipulator 30 are springy in the nature of tweezers. To securely hold the tip portions of the manipulator in their engagement with the lens body, a strip or band 34, which may be resilient, surrounds the prong members 26 and 27 and thus maintains the tips 29 and 31 substantially immovable in the locked position as shown in FIG. 8. If the orientation of the tips and the complementary grooves is such that the tips are lodged more securely therein if the prongs are biased outwardly, the strip 34 may be replaced by a spacer member placed between the prongs to urge them away from each other. The haptics of the lens construction are pulled by a string in the same manner as shown in FIG. 6. However, instead of providing a catch for the looped end of the string member on the lens body as shown in FIG. 6, the looped end 36 of the string is held in a catch member 37 on the manipulator. The whole assembly, as shown in FIG. 11, is placed in a container or box generally indicated by reference numeral 39 and may be sold within the container in sterile condition. While the assembly of FIG. 11 is shown with the haptics in loaded condition, the assembly may be packaged with the string properly looped but with the haptics in their normal, expanded position. The loading is then effected by the surgeon.

During surgery, the surgeon opens the box 39 and removes therefrom the lens assembly by gripping it at the handle portion 28 of the manipulator. If the haptics are in their expanded position, he will pull the string to load them, with the end of the string then engaging the catch 37. After the lens has been inserted into the eye through, for example, a small corneoscleral incision and, when applicable, through the pupil, and the lens body has been positioned by the surgeon by way of the manipulator still attached to the lens body, for example, behind the pupil in the posterior chamber, the surgeon then disengages the looped end of the string and slowly releases the haptics into their expanded position until they are lodged against the eye tissue, permanently to fixate the lens implant. As stated, the surgeon may again "pull in" the haptics if relocation is desired. The string is then cut and removed. This results in a condition essentially as shown in FIG. 9 except that the haptics now bear against the eye tissue and adapt themselves to the surrounding configuration thereby to fix the lens construction. After the lens construction has been securely positioned within the eye, the surgeon cuts the strip or band 34, resulting in slight outward movement of the springy prong members so that the angular tip portions of the prongs slip out from their meshing engagement with the indentations 22, 23 in the lens body, as shown in FIG. 10. If a spacer member is provided instead, as mentioned above, the latter is pushed out, whereupon the tips will disengage from the grooves.

Figure 12:
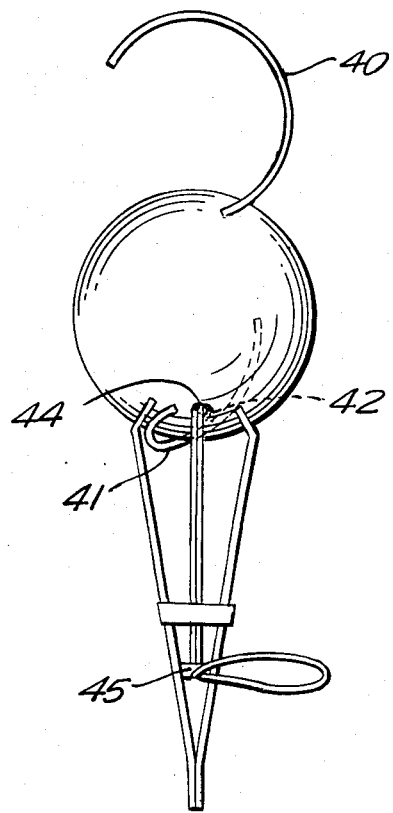
FIG. 12 shows a lens construction with two haptics, only one of which is subject to the loading procedure by means of the string and manipulator.

FIG. 12 shows an embodiment similar to FIG. 8 wherein, however, a lens construction is used with two angularly spaced haptics, only one of which is subject to the loading manipulation. It will be noted that the free haptic 40 extends away from the lens body while the other haptic 41 is pulled by a string through the eyelet 42 and the hole 44, the loop end of the string being held in the catch member 45 on the manipulator. In using this embodiment, the eye surgeon will insert the lens construction with the free haptic first to find a suitable seat within the eye for the haptic, whereafter, the eye surgeon may release the second haptic by means of the manipulation with the string in a suitable manner and as explained above, to seat the lens construction as desired.

It will be appreciated that the manipulator could be detachably attached to the lens body in different ways and/or could have different shapes and forms and constructions without affecting the general spirit of the invention.

What is claimed is:

1. An intraocular lens comprising:
   (a) a lens adapted for intraocular insertion and positioning and being comprised of:
      (i) a lens body, and
      (ii) a plurality of flexible haptics, each of said haptics having a free end portion and a connected end portion permanently and directly secured to the lens body adjacent its periphery, the free end portions of said haptics normally extending away from said periphery of the lens body and being angularly spaced around said periphery; and
   (b) means for maintaining said flexible haptics, prior and during said insertion, in a compressed or loaded position substantially within the space defined by the periphery of said lens body and close to one of the surfaces of said lens body, said periphery, except for said haptics, being devoid of any projections extending away from said periphery whereby, when said haptics are in said loaded position, the overall size of said lens assembly is reduced and insertion of said lens assembly into the eye facilitated, said maintaining means comprising a string, each of said haptics having an eyelet member between said free and connected end portions, said string being looped through the eyelet member of each of the haptics and being capable of being pulled so that the free end portions of all of said haptics are drawn into said space defined by the periphery of said lens body, catch means provided on said lens body for detachably holding said string in its pulled condition, said lens body having at least one hole adjacent its periphery, said string extending through said hole.

2. An intraocular lens as claimed in claim 1, wherein said plurality of flexible haptics comprises three arcuate haptics, equiangularly spaced around the periphery of said lens body.

3. A prepackaged intraocular lens assembly comprising:
   (a) a lens adapted for intraocular insertion and positioning, and having:
      (i) a lens body, and
      (ii) three flexible haptics, each of said haptics having a free end portion and a connected end portion directly secured to the lens body adjacent its periphery, the free end portions of said haptics normally extending away from the periphery of the lens body and being equiangularly spaced around said periphery; each of said three haptics being provided with an eyelet member; and
   (b) a string looped through said eyelet members, said string being capable of being pulled so that each of the free end portions of said haptics is drawn into the space defined by the periphery of said lens body and close to one of the surfaces of said lens body, and catch means on said lens body for detachably holding said string in its pulled condition, said periphery, except for said haptics, being devoid of any projections extending away from said periphery.

4. A prepackaged intraocular lens assembly as claimed in claim 3, further comprising a casing containing said assembly in sterile condition with the haptics extending away from the lens body.

5. A prepackaged intraocular lens assembly as claimed in claim 3, further comprising a casing containing said assembly in sterile condition with the string in pulled condition.

6. A prepackaged intraocular lens assembly comprising in combination:
   (a) a lens adapted for intraocular insertion and positioning and having:
      (i) a lens body, and
      (ii) a plurality of flexible haptics, each of said haptics having a free end portion and a connected end portion directly secured to the lens body adjacent its periphery, the free end portions of said haptics normally extending away from the periphery of the lens body and being angularly spaced around said periphery, said periphery, except for said haptics, being devoid of any projections extending away from said periphery.

(b) a manipulating member detachably attached to said lens body near its periphery for manipulating said lens during said insertion and positioning, (c) said manipulating member comprising a string, each of said haptics having an eyelet member between said free and connected end portions, said string being looped through the eyelet member of each of the haptics and being capable of being pulled so that the free end portions of all of said haptics are drawn into the space defined by the periphery of said lens body, catch means provided on said manipulating member for detachably holding said string in its pulled condition, said lens body having at least one hole adjacent its periphery, said string extending through said hole.

7. A prepackaged intraocular lens assembly as claimed in claim 6, wherein said manipulating member comprises a springy two-pronged handle portion having angularly oriented lens engagement tips at one end, said lens body having slot-like tip-receiving indentations complimentarily oriented to said tips, said tips being detachably engaged in said indentations.

8. A prepackaged intraocular lens assembly as claimed in claim 7, further comprising biasing means on said handle portion for biasing said tips into engagement in said indentations.

9. A prepackaged intraocular lens assembly as claimed in claim 8, wherein said biasing means is a strip member surrounding the prongs of said handle member and urging them towards each other, said tips being detachable from said indentations upon removal of said strip member.

10. A prepackaged intraocular lens assembly comprising in combination:
(a) a lens adapted for intraocular insertion and positioning and having:
(i) a lens body, and
(ii) at least three flexible haptics, each of said haptics having a free end portion and a connected end portion permanently secured to the lens body near its periphery, the free end portions of said haptics normally extending away from the periphery of the lens body and being angularly spaced around said periphery, each of said haptics having a string engaging portion; and
(b) a manipulating member having a two-pronged springy handle portion and lens engaging tips at one end of the handle portion, said lens body having tip-receiving cutouts oriented complimentarily to the tips of said handle portion, said tips being detachably received in said cutouts, and
(c) a string looped through said string engaging portions of the haptics and being capable of being pulled so that the free end portions of the haptics are drawn into the space defined by the periphery of the lens body, and a catch member on said handle portion of the manipulating member, said catch member detachably holding said string in its pulled condition.

11. A prepackaged intraocular lens assembly as claimed in claim 10, further comprising a removable biasing member on said handle portion for biasing said tips into engagement in said cutouts, and a casing accommodating said assembly in sterile condition with the haptics in their normally extended position.

12. A prepackaged intraocular lens assembly as claimed in claim 10, further comprising a removable biasing member on said handle portion for biasing said tips into engagement in said cutouts, and a casing accommodating said assembly in sterile condition with the string in its pulled condition with the catch holding the string in the pulled condition.

13. An intraocular lens comprising:
(a) a lens adapted for intraocular insertion and positioning and being comprised of:
(i) a lens body, and
(ii) a plurality of flexible haptics, each of said haptics having a free end portion and a connected end portion permanently secured to the lens body adjacent its periphery, the free end portions of said haptics normally extending away from said periphery of the lens body and being angularly spaced around said periphery; and
(b) means for maintaining said flexible haptics, prior and during said insertion, in a compressed or loaded position substantially within the space defined by the periphery of said lens body and close to one of the surfaces of said lens body, whereby, when said haptics are in said loaded position, the overall size of said lens assembly is reduced and insertion of said lens assembly into the eye facilitated, said maintaining means comprising a string, each of said haptics having an eyelet member between said free and connected end portions, said string being looped through the eyelet member of each of the haptics and being capable of being pulled so that the free end portions of all of said haptics are drawn into said space defined by the periphery of said lens body, and catch means provided on said lens body for detachably holding said string in its pulled condition, said string being controllably releasable from said catch means so that the operator can selectively and reversibly pull said string for holding it in the catch means and release the string to permit the haptics to expand.

14. An intraocular lens as claimed in claim 13, wherein said lens body has a hole adjacent to its periphery, said string extending through said hole.

15. A prepackaged intraocular lens assembly comprising in combination:
(a) a lens adapted for intraocular insertion and positioning and having:
(i) a lens body, and
(ii) a plurality of flexible haptics, each of said haptics having a free end portion and a connected end portion directly secured to the lens body adjacent its periphery, the free end portions of said haptics normally extending away from the periphery of the lens body and being angularly spaced around said periphery, said periphery, except for said haptics, being devoid of any projections extending away from said periphery.
(b) a manipulating member detachably attached to said lens body near its periphery for manipulating said lens during said insertion and positioning,
(c) a maintaining means comprising a string, each of said haptics having an eyelet member between said free and connected end portions, said string being looped through the eyelet member of each of the haptics and being capable of being pulled so that the free end portions of all of said haptics are drawn into the space defined by the periphery of said lens body, catch means provided on said manipulating member for detachably holding said string in its pulled condition, said string being controllably releasable from said catch means so that the operator can selectively and reversibly pull said string for holding it in the catch means and release the string to permit the haptics to expand.

16. An intraocular lens as claimed in claim 15, wherein said lens body has a hole adjacent to its periphery, said string extending through said hole.

17. An intraocular lens comprising:
(a) a lens adapted for intraocular insertion and positioning and being comprised of:
 (i) a lens body, and
 (ii) a plurality of flexible haptics, each of said haptics having a free end portion and a connected end portion permanently secured to the lens body adjacent its periphery, the free end portions of said haptics normally extending away from said periphery of the lens body and being angularly spaced around said periphery; and
(b) means for maintaining said flexible haptics, prior and during said insertion, in a compressed or loaded position substantially within the space defined by the periphery of said lens body and close to one of the surfaces of said lens body, whereby, when said haptics are in said loaded position, the overall size of said lens assembly is reduced and insertion of said lens assembly into the eye facilitated,
 said maintaining means comprising a catch-like indentation in the lens body adjacent its periphery for each of the haptics, said free end portions of said haptics being capable of engaging in said indentations to be detachably held therein.

18. An intraocular lens comprising:
(a) a lens adapted for intraocular insertion and positioning and being comprised of:
 (i) a lens body, and
 (ii) a plurality of flexible haptics, each of said haptics having a free end portion and a connected end portion permanently secured to the lens body adjacent its periphery, the free end portions of said haptics normally extending away from said periphery of the lens body and being angularly spaced around said periphery; and
(b) means for maintaining said flexible haptics, prior and during said insertion, in a compressed or loaded position substantially within the space defined by the periphery of said lens body and close to one of the surfaces of said lens body, whereby, when said haptics are in said loaded position, the overall size of said lens assembly is reduced and insertion of said lens assembly into the eye facilitated,
 said maintaining means being in the form of a hole for each of the haptics, said holes being provided in the lens body near its periphery, the free end portion of each of the haptics having a protrusion capable of snapping into the respective hole for detachable engagement by the walls thereof.

19. An intraocular lens comprising:
(a) a lens adapted for intraocular insertion and positioning and being comprised of:
 (i) a lens body, and
 (ii) a plurality of flexible haptics, each of said haptics having a free end portion and a connected end portion permanently and directly secured to the lens body adjacent its periphery, the free end portions of said haptics normally extending away from said periphery of the lens body and being angularly spaced around said periphery; and
(b) means for maintaining at least one of said flexible haptics, prior and during said insertion, in a compressed or loaded position substantially within the space defined by the periphery of said lens body and close to one of the surfaces of said lens body, said periphery, except for said haptics, being devoid of any projections extending away from said periphery whereby, when said haptic is in said loaded position, insertion of said lens assembly into the eye is facilitated, said maintaining means comprising a string, at least said one of said haptics having an eyelet member between said free and connected end portions, said string being looped through the eyelet member of the haptic and being capable of being pulled so that the free end portion of said haptic is drawn into said space defined by the periphery of said lens body, catch means provided on said lens body for detachably holding said string in its pulled condition, said lens body having at least one hole adjacent its periphery, said string extending through said hole.

20. A prepackaged intraocular lens assembly comprising in combination:
(a) a lens adapted for intraocular insertion and positioning and having:
 (i) a lens body, and
 (ii) a plurality of flexible haptics, each of said haptics having a free end portion and a connected end portion directly secured to the lens body adjacent its periphery, the free end portions of said haptics normally extending away from the periphery of the lens body and being angularly spaced around said periphery, said periphery, except for said haptics, being devoid of any projections extending away from said periphery,
(b) a manipulating member detachably attached to said lens body near its periphery for manipulating said lens during said insertion and positioning,
(c) said manipulating member comprising a string, at least one of said haptics having an eyelet member between said free and connected end portions, said string being looped through the eyelet member of said one haptic and being capable of being pulled so that the free end portion of said haptic is drawn into the space defined by the periphery of said lens body, catch means provided on said manipulating member for detachably holding said string in its pulled condition, said lens body having at least one hole adjacent its periphery, said string extending through said hole.

* * * * *